(12) United States Patent
Vantroostenberghe

(10) Patent No.: US 7,104,975 B2
(45) Date of Patent: Sep. 12, 2006

(54) MALE URINARY SYSTEM

(76) Inventor: Jacquelin A. Vantroostenberghe, 205 W. Travis St., Holland, TX (US) 76534-9998

(*) Notice: Subject to any disclaimer, the term of this patent is extended or adjusted under 35 U.S.C. 154(b) by 0 days.

(21) Appl. No.: 10/085,493

(22) Filed: Feb. 27, 2002

(65) Prior Publication Data
US 2003/0163102 A1 Aug. 28, 2003

(51) Int. Cl.
*A61F 5/44* (2006.01)
*A47K 11/00* (2006.01)

(52) U.S. Cl. .................. 604/350; 604/346; 604/347; 604/349; 604/355; 4/144.1

(58) Field of Classification Search ............... 604/346, 604/347, 349, 350, 317, 327, 348, 351, 352, 604/353, 355, 356; 4/454, 114.1, 463, 144.1–144.4, 4/466
See application file for complete search history.

(56) References Cited

U.S. PATENT DOCUMENTS

| 1,015,905 | A | * | 1/1912 | Northrop | 604/350 |
| 1,490,793 | A | * | 4/1924 | Ajamian et al. | 604/350 |
| 2,310,505 | A | * | 2/1943 | Blackburn et al. | 604/350 |
| 3,526,227 | A | * | 9/1970 | Appelbaum | 604/350 |
| 4,626,250 | A | * | 12/1986 | Schneider | 604/352 |
| 6,117,120 | A | * | 9/2000 | Heininger | 604/349 |
| 6,679,867 | B1 | * | 1/2004 | Miskie | 604/349 |

* cited by examiner

Primary Examiner—Tatyana Zalukaeva
Assistant Examiner—Michael G. Bogart
(74) Attorney, Agent, or Firm—Marcus Hammack

(57) ABSTRACT

The invention is of a male urinary system which, at its heart, includes a penis/urinary collection interface unit of a design which both collects urine without significant backflow during or after use and is sized and shaped for easy maneuvering into position, even when encountering restrictive spaces caused by body casts, braces, etc. Because the penis/urinary collection interface unit does not itself serve as the urine collection receptacle, but is merely in fluid communication therewith by a length of conduit, the collected urine will, if the system is used as intended, sit safely at a distance on the floor next to the patient's bed, or suspended from a hanging device or bracket attached to the patient's bed.

2 Claims, 2 Drawing Sheets

MALE URINARY SYSTEM

BACKGROUND OF THE INVENTION

1. Field of the Invention

The present invention relates to devices and apparatuses for assisting males in urination.

2. Background Information

Urination can be difficult, messy, and (under circumstances requiring assistance) embarrassing when one cannot use a conventional toilet facility in the conventional manner. All of these factors are greatly amplified when the individual is, for example, a male in his teens, who is bed-ridden because of an accident and is tended (as still is normally the case) by female care givers.

The subject invention arose from a situation involving a boy in his early teens who, after a tragic accident, was bed ridden in a body cast for an extended period of time. For a time, urination was something he avoided until he could avoid it no longer. Having to receive assistance from his female relatives (the only ones usually available for his care) was excruciatingly embarrassing for this young patient.

The boys parents looked in vane for some device or system which would allow their son to urinate without direct assistance. Nothing effective could be found, even when involving the resources and ideas of fellow staff members at the hospital where the boy's mother (and the present inventor) worked.

The primary problem thus far unaddressed by the urinary devices and systems of the prior art relate to allowing a boy or man to urinate while lying substantially on his back, but without having any back flow through whatever tubing or conduit is involved in receiving the urine. Of course, the use of conventional bed pans is virtually out of the question for such a patient, so literal ability to use is beyond the realm of a mere "problem" with such conventional approaches.

Additional deficiencies in the prior art devices and systems relate to ease of managing the collection and disposal of urine. Male urinals, as they are known, are usually unitary structures which, essentially, are receptacles with an opening (sometimes which an short conduit extending from one margin). Therefore contrary to OSHA and other applicable regulations, the urinal is often placed on a nearby table, or on the bed beside the patient immediately after use.

In addition, the bulk of such devices as were just described is such that they cannot be maneuvered into place when dealing with restrictive casts, braces, etc. Situations such as this often require that a patient resort to the use of adult diapers.

It would be highly beneficial, and, not to exaggerate to any real degree, outright humane to provide an improved male urinary device or system which allowed a male patient to urinate without assistance, to provide for effective collection of urine without significant back flow, to address the objective of collecting urine remotely from the patient, table surfaces or the bed itself.

SUMMARY OF THE INVENTION

In view of the foregoing, it is an object of the present invention to provide an improved male urinary assistance device.

It is an object of the present invention to provide an improved male urinary assistance device, which allows use by prone patients without significant backflow during or after use.

It is an object of the present invention to provide an improved male urinary assistance device, which is configured for maneuvering the actual penis/collection system interface into tight spaces created by casts, braces, and the like, by separating the collection receptacle from the interface.

It is an object of the present invention to provide an improved male urinary assistance device, which includes a collection receptacle separate from the penis/collection system interface, thereby obviating the need to place the receptacle on table top or bed surfaces during or after use.

It is an object of the present invention to provide an improved male urinary assistance device, which is easily used by persons which neural motor control disorders.

In satisfaction of these and related objects, the present invention provides an improved male urinary system which, at its heart, includes a penis/urinary collection interface unit of a design which both collects urine without significant backflow during or after use and is sized and shaped for easy maneuvering into position, even when encountering restrictive spaces caused by body casts, braces, etc. Because the penis/urinary collection interface unit does not itself serve as the urine collection receptacle, but is merely in fluid communication therewith by a length of conduit, the collected urine will, if the system is used as intended, sit safely at a distance on the floor next to the patient's bed, or suspended from a hanging device or bracket attached to the patient's bed.

Because the present system is modular in nature, with varying configurations for users with differing needs, the system is easily modified to an almost "custom" design level.

The present designs are of relatively inexpensive, disposable plastic construction, and are, therefore, economical to provide to patients.

In addition to the medical uses described above, the present system can also have considerable utility for airplane pilots who, for lack of restroom facilities on-board, or because of recent security rules which prevent pilot egress from the cockpit, can benefit from the considerable ease of use of this urinary system in the tight confines of an aircraft cockpit. Much the same is true of long-haul truck drivers who prefer not to stop driving, until or unless it is absolutely necessary.

DETAILED DESCRIPTION OF THE PREFERRED EMBODIMENT

Figure 1:
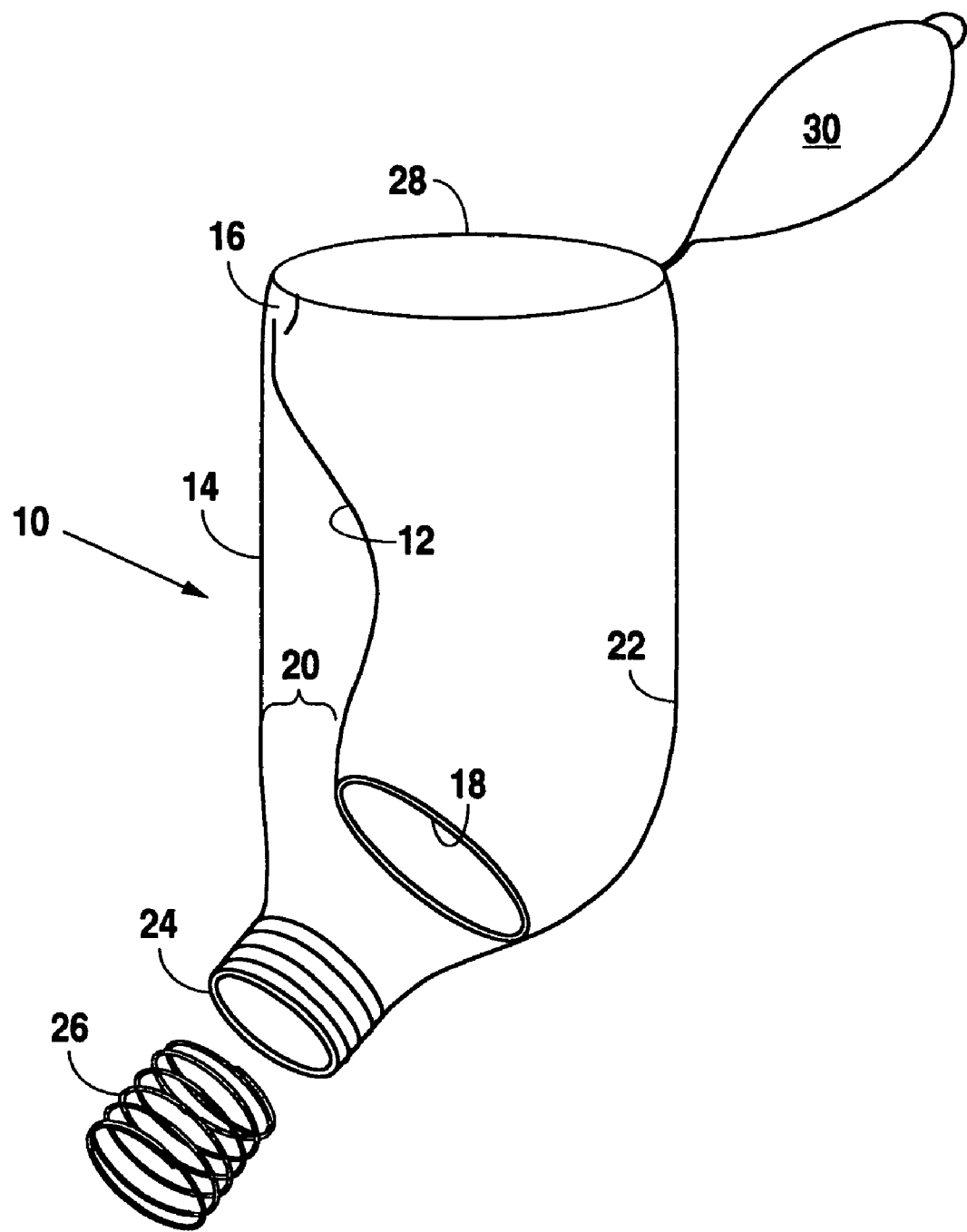
FIG. 1 is a perspective view of a first embodiment of the penis/urinary collection interface unit of the present system.

Referring to FIG. 1, the penis/urinary collection interface unit of the present invention is identified by the reference numeral 10. While variations on the construction details will be apparent to persons reasonably skilled in the design and construction of plastic articles, any penis/urinary collection interface unit 10 within the present invention will include a primary receiver unit 12, and a secondary containment unit 14. Primary receiver unit 12 is contoured at its proximal end 16 for receiving the penis of a user, and when pressed into position, to accommodate the nearby scrotal structure.

At least a portion of the primary receiver unit is, in the preferred embodiment, nested within the secondary containment unit 14. At the distal end 18 of the primary receiver unit 12, the primary receiver unit narrows to allow a gap 20 between the outer surface of of primary receiver unit 12 and the inner surface of secondary containment unit 14.

The gap is preferentially oriented where it will be in the most downward position when positioned as is expected during normal use (that is, with the enlarged, proximal portion of the primary receiver unit in position for accommodating the scrotum). As will be apparent from an examination of FIG. 1, because the margins of primary receiver unit 12 and secondary containment unit 14 are fused, urine, collected in gap 20, cannot spill from penis/urinary collection interface unit 10 (unless is fills to a point of overflowing—not something which was experienced in prototype tests).

The structure of penis/urinary collection interface unit 10 is such that, even when used by a man or boy lying on his back, urine is projected against the upper wall 22 of primary receiver unit 12, is diverted toward the distal terminus 24 of secondary containment unit 14 and flows out of penis/urinary collection interface unit 10 into a conduit 26 which is in sealed fluid communication with penis/urinary collection interface unit 10. Any urine that does not reach and travel through the distal terminus 24 of penis/urinary collection interface unit 10 is harmlessly collected in gap 20 as described above.

In certain embodiments of the present invention, the proximal margin 28 of primary receiver unit 12 is contoured so as not to present a sharp edge to the user. In the alternative, a soft, gasket-like material can be fitted to the margin, both to insure comfort of use, and to provide something of a fluid seal.

Figure 2:
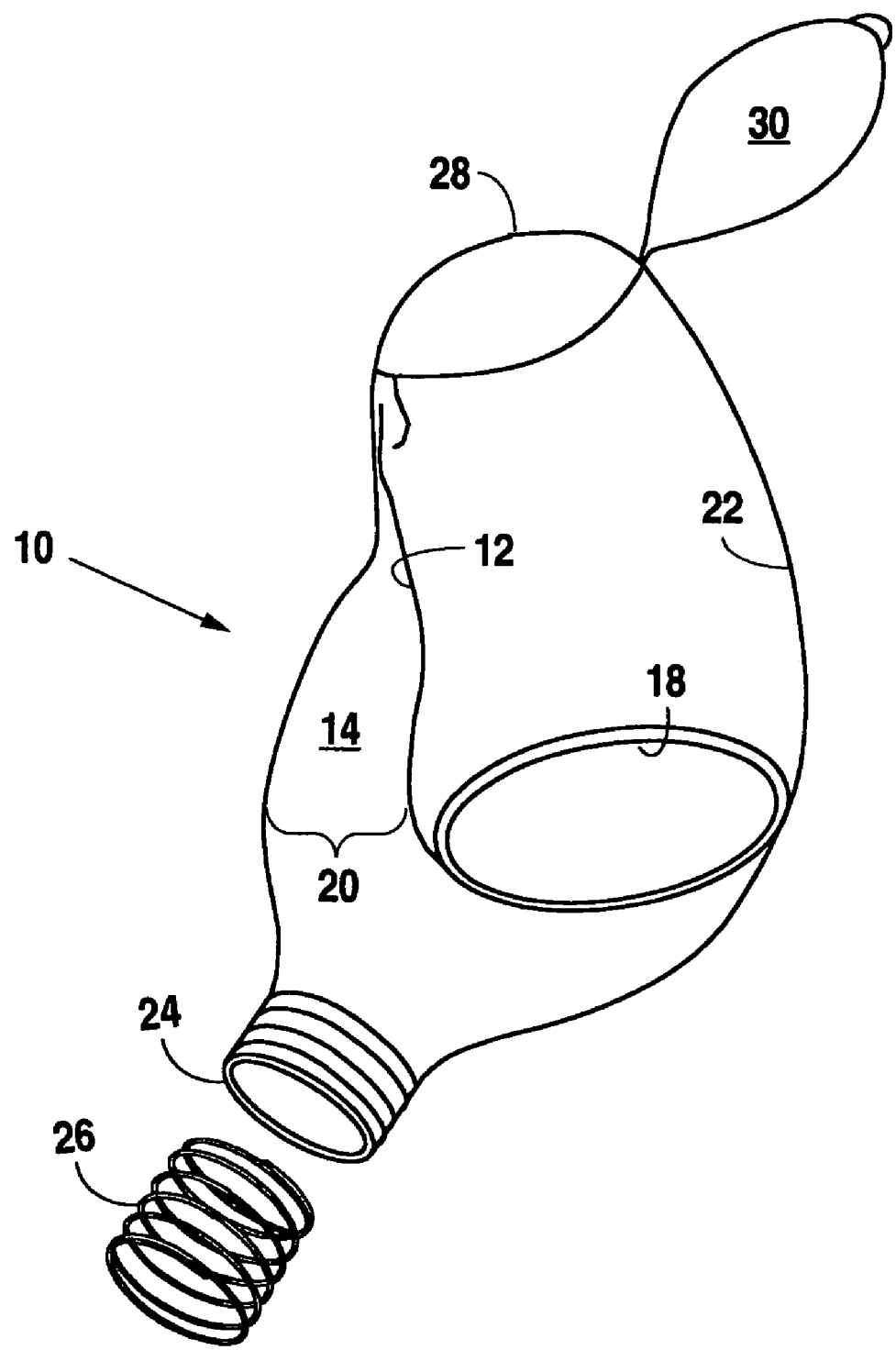
FIG. 2 is a perspective view of an alternative embodiment of the penis/urinary collection interface unit of the present invention, one designed for use by patients in a predominantly supine position.

The embodiment of penis/urinary collection interface unit 10 shown in FIG. 1 has been shown adequate for patients who are either standing or sitting. The version shown in FIG. 2 involves relative orientation of primary receiver unit 12 and secondary containment unit 14 such that urine of most effectively collected and back flow minimized.

To provide the most spill-free use possible, all preferred embodiments of the present male urinary system include snap-fit lids 30 which close and substantially seal the penis/urinary collection interface unit 10 between uses.

Conduit 26, as already shown, attaches, at its proximal end, to the distal end of penis/urinary collection interface unit 10. The distal end of conduit 26 (not shown in the drawings) extends to a collection receptacle (not shown in the drawings) which will be, in any preferred embodiment, easily disconnected from conduit 26 for disposal of collected urine. The design and structure of such a receptacle can be quite varied, the most significant feature simply being its remoteness from the patient and the surrounding surfaces of sanitary concern.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

I claim:

1. A male urinary system comprising:
    a penis/urinary collection interface unit, said penis/urinary collection interface unit comprising a primary receiver unit for accommodating a male penis during urination, configured for juxtaposition to and temporary seating against the adjacent pubic area and comprised of substantially rigid material, and a secondary containment unit wherein said primary receiver unit is at least partially nested within proximal margins of said secondary containment unit and said primary receiver unit being fused to said secondary containment unit to prevent fluid ingress or egress past a line of fusion between said primary receiver unit and said secondary containment unit, said primary receiver unit being positioned relative to said secondary containment unit whereby a gap is formed between the outer surface of said primary receiver unit and the inner surface of said secondary containment unit, said gap extending at least from the distal end of said primary receiver unit and said line of fusion between said secondary containment unit and said primary receiver unit, said primary receiver unit opening at its distal end into said secondary containment unit near the distal end of said secondary containment unit;
    a conduit means attached to said distal end of said secondary containment unit for collecting urine flowing from said distal end of said primary receiving unit;
    a urine receptacle means for receiving urine which flows through and from said conduit; and
    a secondary spill proof mechanism where a proximate end of said primary receiver unit receiving the penis has an elevated edge at the juxtaposition with said pubic area rising from said line of fusion, said elevated edge being configured to facilitate prevention of even minor backflow.

2. The male urinary system of claim 1 further comprising a snap fit lid in combination with said primary receiver unit which closes and substantially seals the penis/urinary collection between uses.

* * * * *